(12) United States Patent
Swinehart et al.

(10) Patent No.: US 8,888,690 B2
(45) Date of Patent: Nov. 18, 2014

(54) CURVED CANNULA (71) Applicant: Intuitive Surgical Operations, Inc., Sunnyvale, CA (US)

(72) Inventors: Charles E. Swinehart, San Jose, CA (US); Theodore W. Rogers, Alameda, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 13/692,339

(22) Filed: Dec. 3, 2012

(65) Prior Publication Data
US 2013/0152657 A1 Jun. 20, 2013

Related U.S. Application Data (62) Division of application No. 12/780,724, filed on May 14, 2010, now Pat. No. 8,343,045.

(60) Provisional application No. 61/321,020, filed on Apr. 5, 2010.

(51) Int. Cl.
*A61B 1/00* (2006.01)
*A61B 17/00* (2006.01)
*A61B 17/34* (2006.01)
*B21D 21/00* (2006.01)
*A61B 19/00* (2006.01)
*A61B 17/29* (2006.01)

(52) U.S. Cl.
CPC .......... *B21D 21/00* (2013.01); *A61B 17/00234* (2013.01); *A61B 2019/462* (2013.01); *A61B 2017/2904* (2013.01); *A61B 17/3421* (2013.01)

USPC .......... 600/184; 72/370.23; 72/369; 604/264

(58) Field of Classification Search
CPC .......... A61B 17/3417; A61B 17/3421; A61B 17/3462; A61B 17/3439; A61M 25/0068; A61M 25/0662; A61M 25/0009; A61M 25/00; A61M 25/0023; A61M 25/0021
USPC ......... 600/184, 185, 188, 196, 199, 220, 221, 600/223; 604/164.11, 264, 272; 606/161; 72/369, 370.04, 370.23, 370.24, 72/370.25, 370.26, 370.12, 370.13
See application file for complete search history.

(56) References Cited

U.S. PATENT DOCUMENTS 3,598,113 A 8/1971 Moore et al.
4,552,554 A 11/1985 Gould et al.
(Continued)

OTHER PUBLICATIONS

PCT/US11/30486 International Search Report and Written Opinion of the International Searching Authority, Jul. 1, 2011, 11 pages.

*Primary Examiner* — Jonathan W Miles (57) ABSTRACT

The cross section of a curved portion of a curved cannula is oval shaped. The oval is oriented such that a major axis of the oval is generally aligned with the curved portion's bend radius. In one aspect, the cannula tube is ovalized so that the radius of curvature of an interior wall approaches the outer radius of an instrument component that contacts the curved portion during instrument insertion. In this first aspect, a wider contact patch area between the instrument component and the cannula results, which reduces friction and stick-slip during insertion. In another aspect, the cannula tube is ovalized so that the radius of curvature of an interior wall is less than the outer radius of an instrument component that contacts the curved portion during instrument insertion. In this second aspect, two contact patches are established between the instrument component and cannula, which also reduces friction and stick-slip during instrument insertion. Also disclosed is a cannula orientation marking that changes circumferential orientation along a length the curved cannula to help a person who is inserting the cannula to properly twist the cannula during insertion.

8 Claims, 6 Drawing Sheets

(56) References Cited

U.S. PATENT DOCUMENTS

| | | |
|---|---|---|
| 4,684,369 A | 8/1987 | Wildemeersch |
| 4,884,558 A | 12/1989 | Gorski et al. |
| 4,930,331 A * | 6/1990 | Manning .................. 72/396 |
| 5,378,241 A | 1/1995 | Haindl |
| 5,509,909 A | 4/1996 | Moy |
| 5,695,513 A | 12/1997 | Johnson et al. |
| 5,728,148 A | 3/1998 | Bostroem et al. |
| 5,803,898 A | 9/1998 | Bashour |
| 5,817,071 A | 10/1998 | DeWindt et al. |
| 6,099,485 A | 8/2000 | Patterson |
| 6,146,371 A | 11/2000 | DeWindt et al. |
| 6,447,484 B1 | 9/2002 | Briscoe et al. |
| 6,645,194 B2 | 11/2003 | Briscoe et al. |
| 7,276,055 B2 | 10/2007 | DeWindt et al. |
| 7,833,156 B2 | 11/2010 | Williams et al. |
| 8,167,867 B2 | 5/2012 | Briscoe et al. |
| 2005/0043682 A1 | 2/2005 | Kucklick et al. |
| 2006/0095059 A1 | 5/2006 | Bleich et al. |
| 2006/0241630 A1 | 10/2006 | Brunnett et al. |
| 2007/0083161 A1 | 4/2007 | Briscoe et al. |
| 2007/0203517 A1 | 8/2007 | Williams et al. |
| 2007/0299387 A1 | 12/2007 | Williams et al. |
| 2008/0033372 A1 | 2/2008 | Briscoe et al. |
| 2008/0306481 A1 * | 12/2008 | Farr et al. .................. 606/79 |
| 2009/0012546 A1 | 1/2009 | N'Diaye et al. |
| 2009/0157076 A1 | 6/2009 | Athas et al. |
| 2009/0216234 A1 | 8/2009 | Farr et al. |
| 2009/0227843 A1 | 9/2009 | Smith et al. |
| 2009/0270676 A1 | 10/2009 | Sicvol |
| 2010/0298839 A1 | 11/2010 | Castro |
| 2011/0071542 A1 | 3/2011 | Prisco et al. |
| 2011/0082456 A1 | 4/2011 | Welt et al. |
| 2011/0230723 A1 | 9/2011 | Castro et al. |

* cited by examiner

CURVED CANNULA

CROSS REFERENCE TO RELATED APPLICATIONS

This application is a continuation of U.S. application Ser. No. 12/780,724 (filed May 14, 2010; disclosing "Curved Cannula"), which issued as U.S. Pat. No. 8,343,045 on Jan. 1, 2013, and claims the benefit of provisional U.S. Patent Application No. 61/321,020 (filed Apr. 5, 2010; disclosing "Curved Cannula"), the entire contents of each of which are incorporated herein by reference.

BACKGROUND

1. Field of Invention

Inventive aspects pertain to minimally invasive surgery, more particularly to minimally invasive robotic surgical systems, and still more particularly to cannulas for minimally invasive robotic surgical systems.

2. Art

Benefits of minimally invasive surgery are well known, and they include less patient trauma, less blood loss, and faster recovery times when compared to traditional, open incision surgery. In addition, the use of robotic surgical systems (e.g., teleoperated robotic systems that provide telepresence), such as the da Vinci® Surgical System commercialized by Intuitive Surgical, Inc. of Sunnyvale, Calif. is known. Such robotic surgical systems may allow a surgeon to operate with intuitive control and increased precision when compared to manual minimally invasive surgeries.

To further reduce patient trauma and to retain the benefits of robotic surgical systems, surgeons have begun to carry out a surgical procedure to investigate or treat a patient's condition through a single incision through the skin. In some instances, such "single port access" surgeries have been performed with manual instruments or with existing surgical robotic systems. What is desired, therefore, are improved equipment and methods that enable surgeons to more effectively perform single port access surgeries, as compared with the use of existing equipment and methods. It is also desired to be able to easily modify existing robotic surgical systems that are typically used for multiple incision (multi-port) surgeries to perform such single port access surgeries.

SUMMARY

A curved cannula includes a curved portion. The curved portion is made to have an oval shaped cross section. The major (long) axis of the oval shape is generally aligned with the cannula's radius of curvature. As a result, a surgical instrument component contacts the interior wall of the cannula tube at a contact patch area that is larger than would exist for a cannula with a circular cross section. Consequently, friction and stiction are reduced as the instrument is inserted through the cannula tube during surgery.

In one aspect the outer radial portion of the curved cannula tube is ovalized to have a radius of curvature that approaches the instrument component's outer circumference, so that the component contacts the curved cannula tube's inner wall at a single contact patch. In another aspect, the outer radial portion of the curved cannula tube is ovalized to have a radius of curvature that is smaller than the instrument component's outer circumference, so that the component contacts the curved cannula tube's inner wall at two contact patches, but not between the two contact patches.

In another aspect, the curved portion is marked on an outer wall to assist the person inserting the cannula. The marking on the outer wall changes circumferential orientation along the length of the cannula so that the person will correctly rotate the cannula during insertion by keeping the marking at the incision towards the surgical site.

DETAILED DESCRIPTION

This description and the accompanying drawings that illustrate inventive aspects and embodiments should not be taken as limiting—the claims define the protected invention. Various mechanical, compositional, structural, electrical, and operational changes may be made without departing from the spirit and scope of this description and the claims. In some instances, well-known circuits, structures, and techniques have not been shown or described in detail in order not to obscure the invention. Like numbers in two or more figures represent the same or similar elements. Diagrammatic figures are intended to be illustrative and are not to scale.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes includes various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

The term "flexible" in association with a mechanical structure or component should be broadly construed. In essence, the term means the structure or component can be repeatedly bent and restored to an original shape without harm. Many "rigid" objects have a slight inherent resilient "bendiness" due to material properties, although such objects are not considered "flexible" as the term is used herein. A flexible mechanical structure may have infinite degrees of freedom (DOF's). Examples of such structures include closed, bendable tubes (made from, e.g., NITINOL, polymer, soft rubber, and the like), helical coil springs, etc. that can be bent into various simple and compound curves, often without significant cross-sectional deformation. Other flexible mechanical structures may approximate such an infinite-DOF piece by using a series of closely spaced components that are similar to "vertebrae" in a snake-like arrangement. In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOF's of relative movement between the links. A short, flexible structure may serve as, and be modeled as, a single mechanical constraint (joint) that provides one or more DOF's between two links in a kinematic chain, even though the flexible structure itself may be a kinematic chain made of several coupled links. Knowledgeable persons will understand that a component's flexibility may be expressed in terms of its stiffness.

In this description, a flexible mechanical structure or component may be either actively or passively flexible. An actively flexible piece may be bent by using forces inherently associated with the piece itself. For example, one or more tendons may be routed lengthwise along the piece and offset from the piece's longitudinal axis, so that tension on the one or more tendons causes the piece to bend. Other ways of actively bending an actively flexible piece include, without limitation, the use of pneumatic or hydraulic power, gears, electroactive polymer, and the like. A passively flexible piece is bent by using a force external to the piece. An example of a passively flexible piece with inherent stiffness is a plastic rod or a resilient rubber tube. An actively flexible piece, when not actuated by its inherently associated forces, may be passively flexible. A single component may be made of one or more actively and passively flexible portions in series.

Inventive aspects are described primarily in terms of an implementation using a da Vinci® Surgical System (specifically, a Model IS3000, marketed as the da Vinci® Si™ HD™ Surgical System), commercialized by Intuitive Surgical, Inc. of Sunnyvale, Calif. Knowledgeable persons will understand, however, that inventive aspects disclosed herein may be embodied and implemented in various ways, including robotic and non-robotic embodiments and implementations. Implementations on da Vinci® Surgical Systems (e.g., the Model IS3000; the Model IS2000, marketed as the da Vinci S® HD™ Surgical System) are merely exemplary and are not to be considered as limiting the scope of the inventive aspects disclosed herein.

Figure 1:
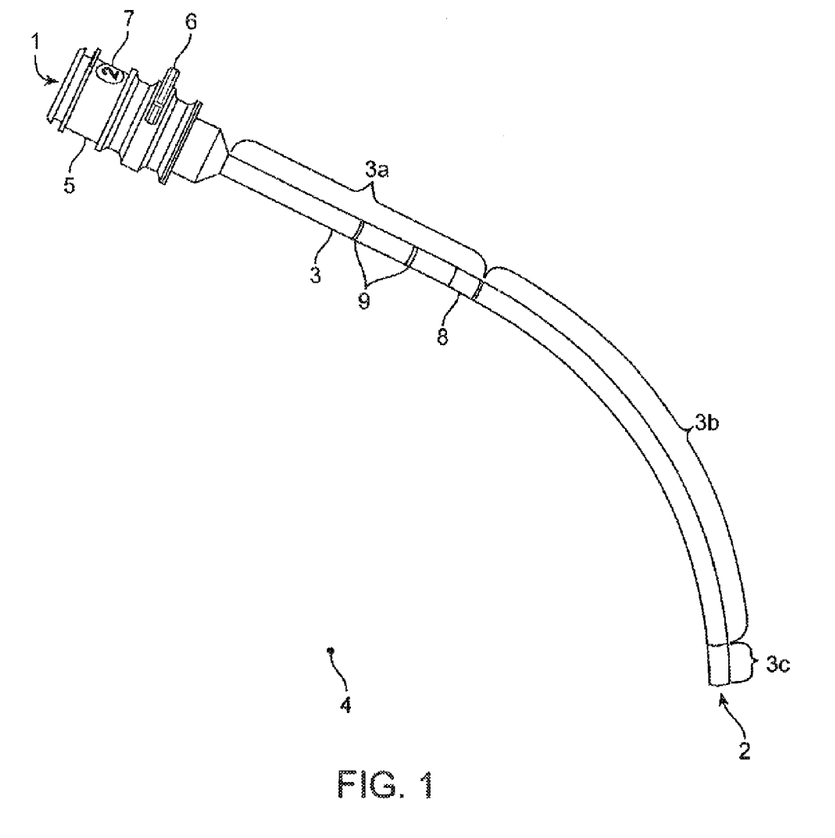
FIG. 1 is a view that illustrates a curved cannula in accordance with one inventive aspect.

FIG. 1 is a view that illustrates a curved cannula in accordance with one inventive aspect. The curved cannula is configured to be used with a da Vinci® Surgical System, commercialized by Intuitive Surgical, Inc. of Sunnyvale, Calif. More specific information about the use of one or more curved cannulas with a teleoperated surgical system, and about aspects of various configurations of the curved cannulas used in such a system, is in U.S. patent application Ser. No. 12/618,583 (filed Nov. 13, 2009; disclosing "Curved Cannula Surgical System"), which is incorporated by reference. Briefly, the curved cannula shown in FIG. 1 has a proximal end 1, a distal end 2, and a cannula tube 3 that extends between the proximal end 1 and the distal end 2. As shown in FIG. 1, the cannula tube includes a proximal straight portion 3a, a middle curved portion 3b, and a distal straight portion 3c. The middle curved portion 3b is curved (bends) at a constant radius in one aspect (other curvatures may be used in other aspects), and the curve is centered on center point 4 (origin of the bend radius). In one implementation, the radius of curvature is about five inches. A longitudinal axis extends from the proximal end of tube 3, through the center of tube 3, to the distal end of tube 3. Thus a plane of curvature is defined by this longitudinal axis and center point 4. It can also be seen that locations on the curved portion that are towards the outside of the curve, farther from center point 4, may be considered distal from center point 4. Likewise, locations on the curved portion that are towards the inside of the curve, nearer to center point 4, may be considered proximal to center point 4. It can be seen that this description can be generalized to include more complex "S" planar tube curvatures or volumetric tube curvatures. For such a generalization, a radius of curvature exists for each location on the curved portion 3b (curved tube's localized bend radius). In one aspect the curved portion is substantially rigid, although it may straighten slightly as a flexible surgical instrument having a relatively high bend stiffness, as discussed below, is inserted through the cannula.

FIG. 1 also shows a mounting feature 5 at the proximal end of the depicted curved cannula embodiment. Much of the interior of mounting feature 5 is removed (e.g., machined out) so as to help guide a flexible surgical instrument into the cannula and to clear space for a proximal end cannula seal (not shown). The depicted mounting feature 5 is configured to be held by robotic surgical system cannula holder associated with a robotic manipulator assembly. Tab 6 on mounting feature 5 acts as an alignment key. The cannula holder's grasping jaws close around mounting feature 5, but not completely, so that tab 6 protrudes between the ends of the jaws in order to properly orient the curved cannula with respect to the robotic manipulator. A cannula identification indicator 7 helps operating room personnel match the particular curved cannula with its associated manipulator. As shown in FIG. 1, for example, the "2" is matched with the manipulator on arm number "2". The orientation between the plane of curvature and the alignment key may be different for a curved cannula associated with another manipulator arm (e.g., arm number "1"), and so it is important that the correct curved cannula be mounted on its associated manipulator arm.

FIG. 1 also shows markings on cannula tube 3. A prominent marking 8 (a wide ring is shown) is placed at the remote center of motion. This marking 8 helps operating room personnel insert the cannula to the proper depth through a patient's body wall so that the remote center of motion is correctly positioned at the body wall. One or more depth markings 9 may be placed on cannula tube 3 to further help operating room personnel insert the cannula to the proper depth (e.g., for patients that have relatively thick body walls due to subcutaneous fat).

Figure 2:
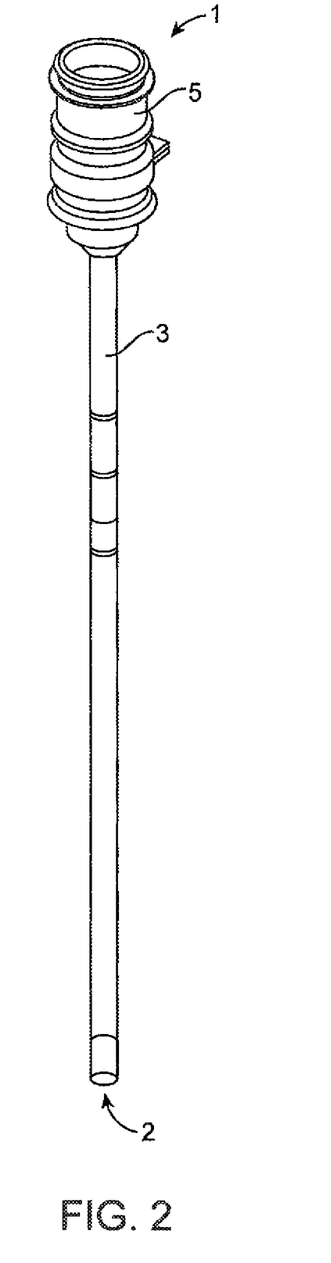
FIG. 2 is another view of the curved cannula embodiment depicted in FIG. 1.

FIG. 2 is another view of the curved cannula embodiment depicted in FIG. 1. In FIG. 2, the cannula is shown with the plane of curvature perpendicular to the page. In FIG. 2 it can be more easily seen that a servo controlled surgical instrument with a flexible shaft can be inserted into the cannula's proximal end 1. The instrument's shaft will extend through the cannula tube 3 and will exit the distal end 2 to be positioned to work at a surgical site within a patient.

Figure 3A:
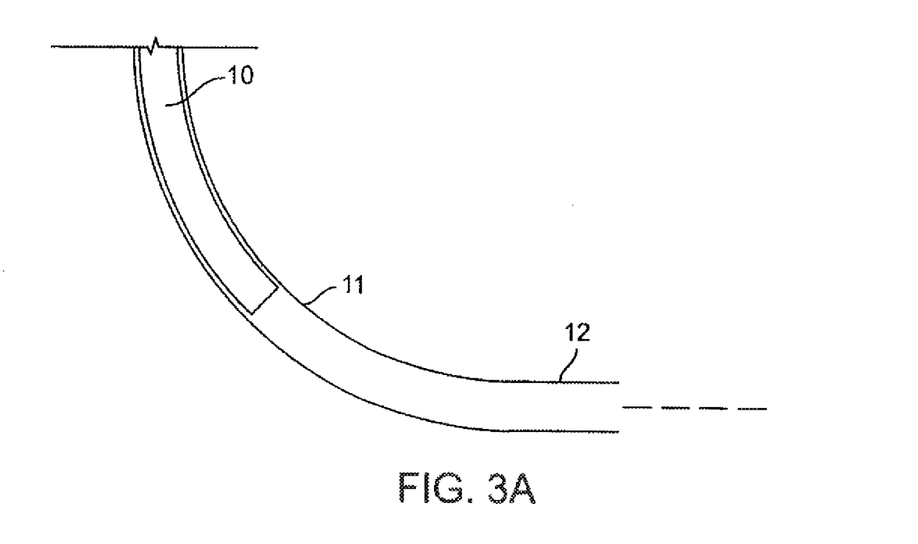
FIGS. 3A and 3B are diagrammatic longitudinal cross sections of curved cannula distal portions that illustrate design considerations.
Figure 3B:
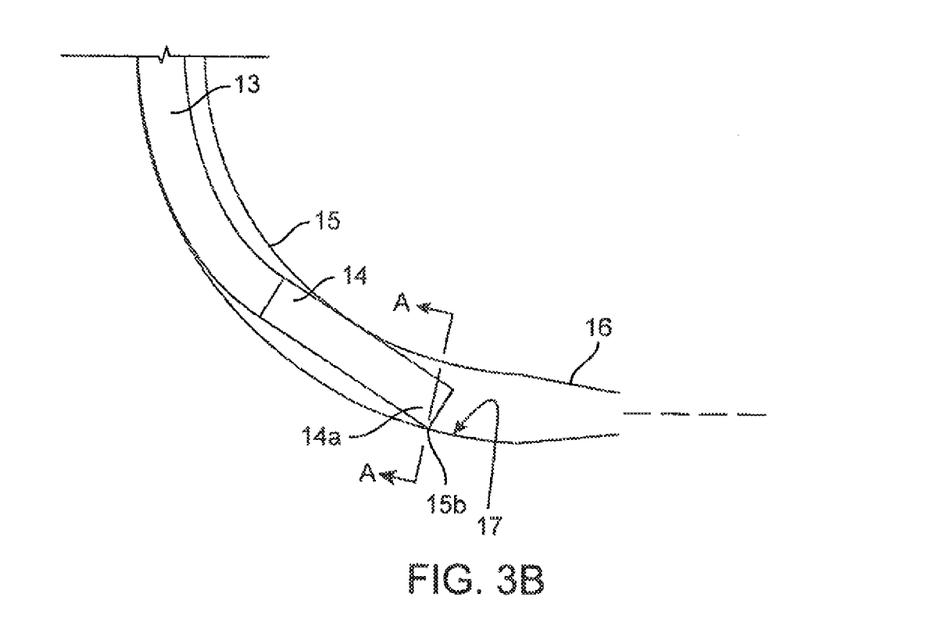

FIGS. 3A and 3B are diagrammatic longitudinal cross sections of curved cannula distal portions that illustrate design considerations. As illustrated in FIG. 3A, a flexible instrument shaft 10 extends part-way through a curved tube portion 11 of a curved cannula. It can be seen that if both the instrument shaft and the interior of the curved tube have circular cross sections, then the tube's inner diameter can be sized close to the shaft's outer diameter. And, a straight distal end extension 12 to the cannula (akin to 3c, FIG. 1), used to direct the shaft in a predicted orientation with reference to the tube's longitudinal centerline axis, can also have an inner diameter sized close to the shaft's outer diameter. But in practice, distal end surgical end effectors are rigid, not flexible, and their length is typically longer (e.g., 3×-4× or more) than the shaft's diameter.

And so, as illustrated in FIG. 3B, for a particular flexible instrument shaft 13 and long, rigid surgical end effector 14 combination, it can be seen that the inner diameter (and correspondingly the outer diameter) of the curved portion of the tube 15 must be made somewhat larger so that the end effector 14 can slide through the curved portion. (In practice, some end effector distal end diameters are smaller than their proximal end diameters, but the principle remains the same.) In addition, a straight distal end extension 16 requires a necked-down inner diameter to direct the shaft and end effector in a predicted orientation with reference to the tube's longitudinal centerline axis.

FIG. 3B further illustrates how a distal portion 14a of the end effector contacts the inner wall 17 of curved tube 15 at a location 15b at the extreme outside radius. Since this contact is at an angle to the tube's inner wall, there can be a considerable contact stress between the end effector and the tube's inner wall as the instrument is initially inserted through the cannula. This contact stress results in high friction, and also stick-slip "stiction", between the end effector and the cannula as the instrument is inserted. As a result, it can be difficult for operating room personnel to insert the instrument through the cannula and to control the insertion velocity when the cannula is placed in the patient's body wall. For example, if a person applies a high insertion force to overcome the stiction between the end effector and the cannula, the instrument may suddenly release and injure the patient if the person is not prepared to immediately release insertion force.

In addition, such contact between the end effector and the cannula, and imperfect surface roughness of each, may cause scraping that results in wear and particulation. For example, scraping between a hard metal end effector and a hard metal cannula may produce metal particles. Alternatively, scraping may occur if one material is hard and one material is soft, so that, for example, a hard cannula may scrape material from a soft end effector clevis.

The considerations that apply to the contact between the end effector and the cannula tube's inner wall during initial insertion may also apply to contact between the instrument shaft and the cannula's inner wall. During telemanipulation, the instrument shaft typically moves within the cannula in many small increments as the surgeon moves the end effector at the surgical site. In order for the instrument to move smoothly during a surgical procedure, it is important to minimize both friction and stiction during instrument insertion and withdrawal movements associated with the surgeon's hand movements. It can be seen that when the instrument's flexible shaft is inserted or withdrawn through the cannula tube, the shaft will tend to rub against either the outermost or innermost radius of the tube's inner wall. If the flexible shaft's bend stiffness is relatively low, the shaft tends to contact the outer radial portion of the tube's inner wall during insertion and the inner radial portion of the tube's inner wall during withdrawal. If the flexible shaft's bend stiffness is relatively higher, such that the shaft tends to return to a generally straight alignment after it has been bent, then the shaft tends to contact the outer radial portion of the tube's inner wall during both insertion and withdrawal. Embodiments of such relatively higher stiffness flexible shafts are shown in U.S. patent application Ser. No. 12/618,583, cited above. A relatively higher shaft stiffness is desirable so that the portion of the shaft that is cantilevered past the cannula's distal end is substantially straight for motion prediction and control, and so that the cantilevered portion resists bending when the surgeon is manipulating tissue.

The instrument shaft's cross section, and in some instances the distal part of the end effector that contacts the inside wall of the curved cannula tube, is typically symmetric around its center (e.g., substantially circular) for the length that extends into and through the curved portion of the cannula, so that the instrument can roll at various insertion depths within the cannula.

Again, it should be understood that the diagrams are illustrative. In practice, the distal-most portion of the end effector that provides the significant contact stress that results in high friction/stiction and possible scraping may be, for example, a portion of a clevis that supports the end effector's working jaws. Skilled artisans will understand that some end effectors, such as Maryland graspers, curved scissors, electrocautery hooks, and the like, are not symmetrical at their distal-most tips. Such instruments may be oriented to match the cannula curvature during instrument insertion, and if the shaft is free to roll they tend to self-rotate to a minimum energy position during instrument withdrawal.

Figure 3C:
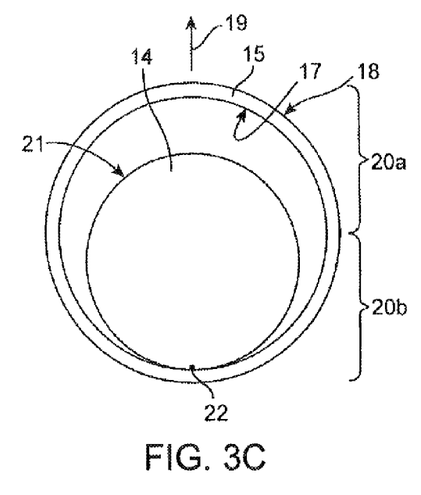
FIG. 3C is a diagrammatic view of a cross section of the curved portion of the cannula tube taken at cut line A-A on FIG. 3B.

FIG. 3C is a diagrammatic view of a cross section of the curved portion of the cannula tube taken at cut line A-A on FIG. 3B. As shown in FIG. 3C, curved cannula tube 15 has an inner wall 17 and an outer wall 18. The tube is curved in the direction shown by arrow 19, so that at any location along the cannula's longitudinal axis the curved portion of the tube may be described as having an inner radial portion 20a closer to (proximal to) the tube's center of curvature and an outer radial portion 20b farther from (distal from) the tube's center of curvature. End effector 14 is shown inside the tube, and the end effector has an outer circumference 21. Since the tube's inner wall 17 and the instrument's outer circumference 21 are both curved (e.g., circular), at least at the location where the two contact, they contact each other at a single small contact patch 22 at location 15b (FIG. 3B). It can be seen that for an elongated contact between a portion of the instrument (e.g., the shaft) and the curved cannula tube's inner wall, this contact patch is illustrative of a single bearing thin linear contact patch between the instrument portion and at least a portion of the tube's inner wall in the cannula's outer radial portion 20b as the instrument is inserted through the cannula. A similar situation may exist in the cannula's inner radial portion 20a as a instrument with relatively low bend stiffness is withdrawn from the cannula, as discussed above. As shown in FIG. 3C, the cross section of the curved cannula tube is circular (the term "circular" used herein in this context meaning truly circular or acceptably nearly circular).

It is well known that as a circular cross section tube is bent, its cross section tends to flatten in the direction of the radius of curvature. This flattening is referred to herein as "ovalization", since the resulting cross sectional shape of a circular cross section tube made of a relatively high strength material (e.g., 304 stainless steel) tends to become oval after bending. The major (long) axis of this oval shape is generally perpendicular to the tube's radius of curvature at each location along the bend. But if the curved portion of the cannula tube is ovalized by this bending, then it can be seen with reference to FIG. 3B that an even larger diameter initially circular cross section tube is needed so that sufficient clearance exists after bending for the end effector to pass through the bent tube.

It is desirable to make the cannula tube's inner diameter fit fairly closely with the instrument shaft's outer diameter, so that the instrument's position is known with reference to the cannula for correct instrument tip positioning at the surgical site. Also, it is desirable that the cannula tube outer diameter be kept small to minimize patient trauma. Thus, the cannula tube is fabricated using known methods to help preserve the tube's circular cross section in the curved portion (e.g., by bending with a stiffening element inserted inside the tube, which is then withdrawn as the tube is bent). Since the use of such methods still results in a slightly ovalized tube cross section, the tube is then further worked to make the cross section circular. In one instance, for example, the curved portion is placed in a mill vise and squeezed. Since the tube material is stiff, this squeezing produces the desired circular cross section. Such a circular cross section results in a relatively small contact patch between instrument and cannula tube, which means that contact stress in this contact patch is high.

And so, it is desirable to reduce contact stress between the end effector and the curved cannula tube during instrument insertion and also to reduce contact stress between the instrument shaft and the curved cannula tube during surgical use. In accordance with aspects of the invention, the effective area of the contact patch between the instrument and the curved tube is increased.

In accordance with an inventive aspect, the cross section of the curved portion of a curved cannula is ovalized beyond restoring the cross section to circular, so that the major (long) axis of the oval shape is generally aligned with the radius of curvature. As used herein, an oval shape generally refers to any off-round shape in which the major axis's length is larger than the minor axis's length, and it includes without limitation ellipses, shapes having only one axis of symmetry (e.g., "egg-shaped" forms), and shapes that include straight sides that join curved ends (e.g., "racetrack-shaped" forms).

Figure 4:
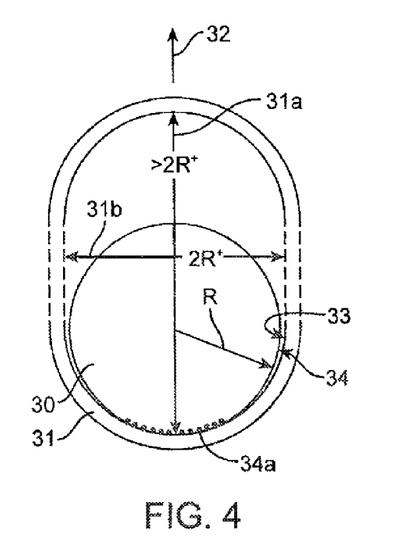
FIG. 4 is a diagrammatic cross-sectional view that illustrates aspects of the invention as an idealized model.

FIG. 4 is a diagrammatic cross-sectional view that illustrates aspects of the invention as an idealized model. FIG. 4 shows an end effector 30 having a circular cross section. End effector 30 is positioned inside a curved cannula tube portion 31. Curved cannula tube portion 31 is curved in the direction shown by arrow 32, so that end effector 30 is positioned in the outer radial portion of tube 31. In this model, the end effector has a radius R, and so the radius of the inner wall 33 of the outer radial portion of tube 31 is also R. Since tube 31 is ovalized so that its major axis 31a is in the direction of curvature, the length of the minor axis 31b of tube 31 is 2R+ (the 2R+ signifies that the minor axis is slightly larger (e.g., one percent) than 2R so that the end effector does not contact the tube's straight sides). The major axis is longer than 2R (longer than 2R+) so that the rigid end effector can pass through tube 31, as discussed above with reference to FIG. 3B. It can be seen that, due to material deformation and surface roughness, the contact patch between the shaft's outer wall 34 and the tube's inner wall 33 extends for a significant fraction of the circumference, as indicated by the line of dots 34a. Therefore, contact stress between the instrument and the cannula is distributed over a large area, which helps to minimize friction/stiction effects and scraping between the two components. Skilled artisans will understand that for real implementations, as the contact pressure (normal force/contact area) increases, at some point one of the surfaces begins to deform, and the coefficient of friction increases. Reducing the contact pressure below this threshold value both reduces the apparent friction/stiction and the wear rate between the parts.

It can also be seen from FIG. 4 that if the instrument shaft is sufficiently stiff so that it generally remains in the outer radial portion of the tube, then the shape of the inner radial portion of the tube does not have to be one that maximizes the contact patch. It should be understood that at the ends of the curved tube, where it joins the proximal and distal straight tube sections, the instrument shaft stiffness tends to bridge across to the cannula's inside wall to minimize the bend angle. For example, the tube's cross section could be asymmetrical (e.g., egg-shaped). But referring once again to FIG. 3B, it can be seen that the inner radial portion should be shaped to allow the end effector to pass while minimizing the cannula tube dimensions.

In contrast to the idealized model presented with reference to FIG. 4, however, in practice the cannula tube need only be ovalized slightly in the direction of the tube's curvature to achieve highly beneficial results. The contact stress between the end effector and the cannula tube causes the tube's cross section to deform under the load. Since neither the end effector nor the tube is infinitely stiff, as the curvature of the outer radial portion of the tube approaches the end effector's outer radius, the contact patch width increases. Thus when comparing a circular cross section cannula against a cannula having an ovalized cross section in accordance with aspects of the invention, where both cannulas offer the same capability to allow a rigid end effector to pass through, the increased contact patch width in the ovalized cannula results in a desirable distribution of the contact stress over a larger area than for the circular cross section cannula.

Figure 5:
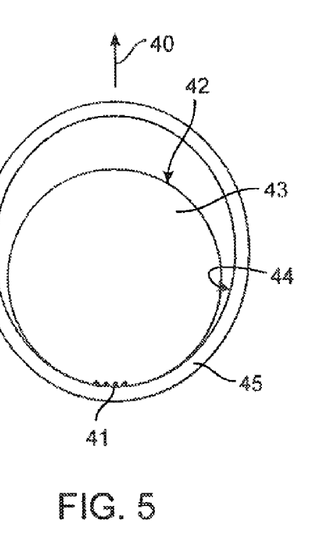
FIG. 5 is a diagrammatic cross-sectional view that illustrates one aspect of an increased contact patch width in a curved cannula tube that is ovalized in the direction of curvature.

FIG. 5 is a diagrammatic cross-sectional view that illustrates one aspect of an increased contact patch width in a curved cannula tube that is ovalized in the tube's direction of curvature, shown by arrow 40. At contact patch 41 between the outer wall 42 of end effector (or instrument shaft) 43 and the inner wall 44 of cannula tube 45, the localized bend radius of inner wall 44 approaches the end effector's local circumferential radius. Due to material deformation and surface roughness, this localized condition increases the area of contact patch 41. As a result, friction/stiction effects between the end effector and the cannula tube are significantly reduced over those encountered with a curved cannula having a circular cross section, so that a flexible shaft instrument is significantly easier to insert though the cannula. And, the particulation risk from scraping is also significantly reduced or eliminated. It can be seen that for an instrument shaft, this condition increases the linear bearing contact patch area between the instrument shaft and the cannula within the curved cannula tube.

Figure 6:
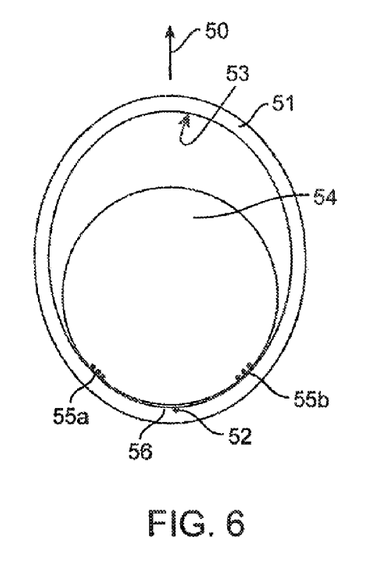
FIG. 6 is a diagrammatic cross-sectional view that illustrates another aspect of increasing the contact patch area between an instrument and a curved cannula tube that is ovalized in the tube's direction of curvature.

FIG. 6 is a diagrammatic cross-sectional view that illustrates another aspect of increasing the contact patch area between an end effector (or instrument shaft) and a curved cannula tube that is ovalized in the cannula tube's direction of curvature, shown by arrow 50. FIG. 6 is illustrative of cannula tube embodiments in which ovalization is carried out so that a localized radius of curvature of the outer radial portion of the tube is smaller than the circular instrument's localized circumference radius. As shown in FIG. 6, curved cannula tube 51 is ovalized so that the radius of curvature at the extreme outer radius 52 of tube 51's inner wall 53—where the contact patch 41 would be in aspects illustrated by FIG. 5—is less than the localized radius of end effector 54. As a result, the end effector contacts the tube's inner wall at two points 55a and 55b. As with the single contact patch aspect described with reference to FIG. 5, localized material deformation and surface roughness will determine the size of each of the two contact patches. Thus the contact stress between the end effector and the tube's inner wall at each of the two linear contact patches is less than the contact stress at a single contact patch for a cannula having a circular cross section, and so friction/stiction effects and scraping between the instrument and the cannula tube are reduced. It can be seen that for the instrument shaft, a similar two-location contact between the shaft and the tube wall may exist for at least part of the tube (i.e., along two bearing linear contact patches rather than along a single bearing linear contact patch as with a circular cross section tube or with a tube having an extreme outer radius of its inner wall is larger than the instrument shaft's radius).

In addition, it can be seen illustrated in FIG. 6 that a small gap 56 exists between the outermost radius of the tube's inner wall and the instrument's inner wall. This gap 56 may provide a small clearance for parts of an instrument's surgical end effector. Thus as the end effector slides through the ovalized curved portion of the cannula, contact and contact force between hard parts of the end effector and the tube's inner wall may be further reduced or in some instances may be avoided.

Figure 7:
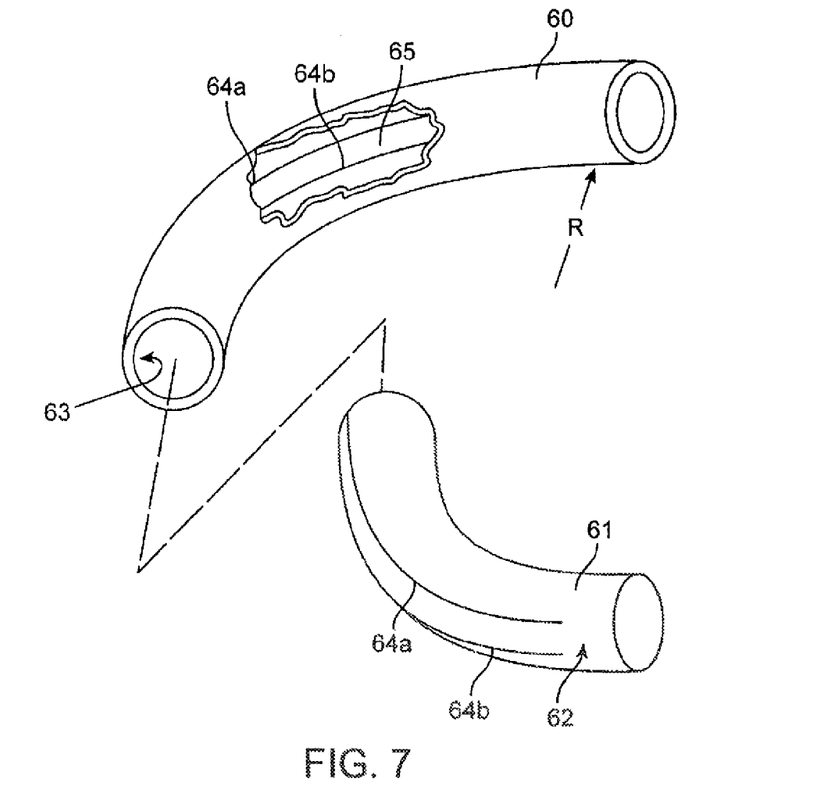
FIG. 7 is a diagrammatic exploded perspective view of a curved portion of a cannula and a curved portion of an instrument shaft.

FIG. 7 is a diagrammatic exploded perspective view that further illustrates inventive aspects. An illustrative section 60 of the curved portion of the curved cannula is shown. The section 60 has a radius of curvature R, as indicated by the depicted arrow. FIG. 7 also shows an illustrative section 61 of a flexible, elongate shaft of a surgical instrument. The elongate shaft is inserted into the curved cannula, and a robotic manipulator (not shown) advances and withdraws the shaft through the cannula during surgery. As disclosed herein, the cross section of the curved portion of the curved cannula is ovalized, the cross section of the instrument shaft is substantially circular, and the two cross sections are sized such that the outer wall 62 of the instrument contacts the inner wall 63 of the curved portion of the cannula along two linear contact patches 64a,64b towards the outside of the cannula/instrument curvature. It can be seen that the contact patches are longitudinal—generally aligned with the cannula's longitudinal axis between proximal and distal ends. Due to the nature of the hardware, such contact may occur along substantially the entire length of the curved portion of the cannula, or the contact may occur at less than the entire length of the curved portion of the cannula along one, two, or more lengths. The linear contact patches act as the main bearing surfaces as the shaft translates through the curved portion, although other incidental contact between the shaft and the cannula's inner wall may occur. FIG. 7 also shows that the outer wall 62 of the instrument shaft does not contact the inner wall 63 of the curved portion of the cannula in the area 65 between the two contact lines. As mentioned above, linear contact patches similar to patches 64a,64b may exist towards the inside of the cannula/instrument curvature. It can also be seen that contact patches 64a,64b illustrate contact patch traces on the tube's inner wall as a rigid end effector passes through, and they illustrate the edges of a single large contact patch trace or linear contact patch as discussed above for end effectors and instrument shafts with reference to FIGS. 4 and 5.

Figure 8:
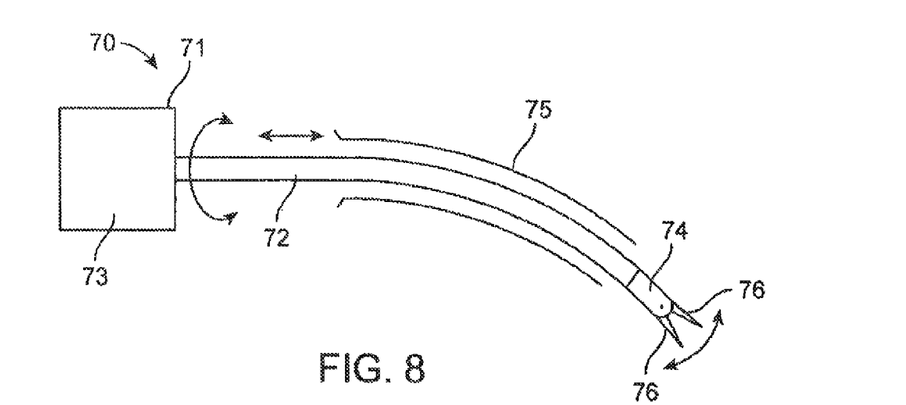
FIG. 8 is a diagrammatic view of an illustrative cannula and instrument assembly.

FIG. 8 is a diagrammatic view of an illustrative cannula and instrument assembly 70. The assembly includes surgical instrument 71 with a flexible, elongate shaft 72. A force transmission mechanism 73 is coupled to the proximal end of shaft 72, and a surgical end effector 74 is coupled to the distal end of shaft 72. The force transmission mechanism receives force/torque from servomotors in a robotic manipulator and redirects the received force/torque to move one or more parts of the instrument. The shaft is inserted through a curved cannula 75 and is rolled and/or inserted/withdrawn within the curved cannula, as indicated by the double-headed arrows, during a surgical procedure. The curved cannula is ovalized as described herein. In some instances one or more jaws 76 of the surgical end effector are moved during surgery, as indicated by the double-headed arrow. Further details of such surgical instruments are disclosed in U.S. patent application Ser. No. 12/618,583, cited above.

Referring back to FIGS. 6 and 7, end effector 74 typically includes rounded surfaces at its outer surfaces. Nevertheless, some more abrupt edges or corners may exist due to end effector design or manufacturing specifications. As mentioned above, these small areas on the end effector may contact and scrape against the curved cannula inner wall surface, depending on the roll orientation of the end effector as it passes through the cannula. But as described herein the contact stress between such end effector components and the curved cannula tube may be reduced. Accordingly, the chance of the end effector scraping against and possibly producing unwanted metal particles from the cannula's inner wall may be reduced or eliminated.

In one implementation, the curved portion of the cannula is ovalized in accordance with inventive aspects by squeezing between jaw surfaces of a mill vise. The curved portion is made of cold worked 304 stainless steel, and so an acceptable oval shape results. Other materials such as Carpenter Custom 465® stainless steel (which may be made harder than 304 stainless steel) may be used. Persons familiar with tube fabrication methods will understand that various other methods of producing an ovalized curved tube exist, such as ovalizing the tube by drawing it through a tooling piece. In one implementation, the curved portion (e.g., 3b, FIG. 1) is fabricated separately from the straight portion (e.g., 3a).

As a result of the ovalization described herein, instrument insertion is significantly smoother than with a curved tube having a circular cross section. Aspects described have been generally directed to use with instruments having a relatively higher bend stiffness, which as discussed above tends to keep the instrument shaft towards the outer radial portion of the curved cannula tube. Persons of skill in the art will understand that similar advantages may be obtained by similarly shaping the curved cannula tube's inner radial portion for use with instruments that contact the inner radial portion.

For each of the ovalized embodiments described herein, a straight distal portion of the cannula may be necked down and returned to a circular cross section, as described above with reference to FIGS. 3A and 3B. In some implementations this necking down is done by inserting a piece into the cannula tube's distal end. Alternative methods, such as swaging a distal straight portion of the tube's diameter down, or welding a conical piece to the distal end of the curved tube, may be used.

It can be appreciated that although inventive aspects have been described in terms of an ovalized shape, other geometric shapes may be used. For example, a cannula tube cross section may have a regular or irregular polygon shape that also provides at least two contact lines between an inner wall of the curved portion of the cannula tube and an instrument shaft extending through the cannula tube. Thus there is a gap between the instrument shaft and the inner wall of the curved portion of the cannula between the or each set of contact lines.

Insertion Orientation Marking

When the cannula is first inserted through the patient's body wall, the insertion is typically done with a twisting motion, often with an obturator inserted through the cannula tube. In addition, once the distal end portion of the curved cannula is inserted, the cannula must be rotated during further insertion to place the cannula's distal end near the surgical site. When portions of the curved cannula are already inserted, however, the person inserting the cannula often has trouble keeping the cannula correctly aligned towards the surgical site during the rest of the insertion.

Figure 9:
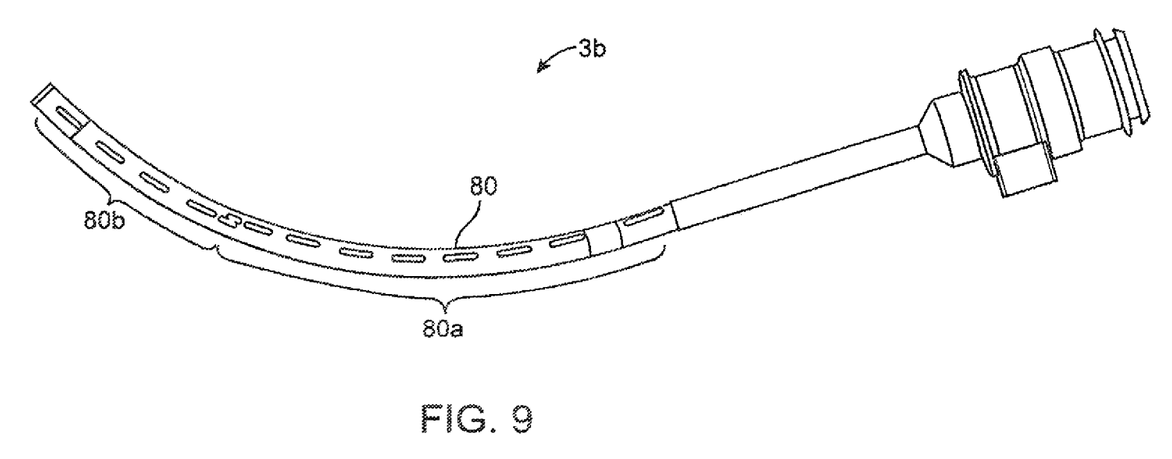
FIG. 9 is a view that illustrates a curved cannula in accordance with another inventive aspect.

FIG. 9 is a view that illustrates a curved cannula in accordance with another inventive aspect. As shown in FIG. 9, the curved cannula includes an insertion orientation marking 80 along the cannula tube. FIG. 9 shows that the orientation marking 80 is in two parts, both heavy dashed lines. A proximal part 80a is shown along a proximal part of the curved cannula portion 3b, and a distal part 80b is shown along a distal part of the curved cannula portion 3b. In FIG. 9 both parts are along a constant radius of the curved cannula portion, but at different rotational positions along the outer wall of the cannula tube. During insertion, the person inserting the curved cannula keeps the insertion mark oriented towards the surgical site (e.g., marked on the patient's body), so that as insertion progresses, the person inserting the cannula will correctly rotate the cannula. Various other markings may be used, and they may be a series of two or more discrete, constant radius lines on the cannula tube, or they may be in a spiral around the tube.

What is claimed is:

1. A method of manufacturing a curved cannula, comprising:
    forming at least a portion of a rigid cannula tube into a curved portion having a bend radius at a particular location, wherein a cross-section at the particular location has an elongated shape with a long axis being generally perpendicular to the bend radius; and
    shaping the cross-section of the curved portion at the particular location into an oval shape, wherein a major axis of the oval shape is generally aligned with the bend radius at the particular location;
    wherein dimensions of the oval shape define at least two spaced apart, discrete contact regions on the oval shape at the particular location, the two contact regions being arranged to contact a surgical instrument when the surgical instrument is received within the tube at the curved portion.

2. The method of claim 1:
    wherein shaping the cross section of the curved portion at the particular location into an oval shape comprises pressing the curved portion between two surfaces.

3. The method of claim 1:
    wherein shaping the cross section of the curved portion at the particular location into an oval shape comprises shaping an inner wall of the cannula at a location where the major axis of the oval shape intersects the inner wall to have a radius of curvature that is smaller than or substantially equal to an outer circumference radius of curvature of a surgical instrument that contacts the curved portion during insertion of the surgical instrument.

4. The method of claim 1:
    wherein forming the curved portion comprises forming a portion of an interior wall of the curved portion of the cannula tube to intersect the major axis distal to an origin of the bend radius of the curved portion of the cannula tube.

5. The method of claim 1:
    wherein forming the curved portion comprises forming a portion of an interior wall of the curved portion of the cannula tube to intersect the major axis proximal to an origin of the bend radius of the curved portion of the cannula tube.

6. The method of claim 1:
    wherein at the cross section of an interior wall of the curved portion of the cannula tube, a length of a minor axis of the cross section is slightly larger than twice a radius of curvature of an outer circumference of a shaft of the surgical instrument.

7. A method of manufacturing a curved cannula, comprising:
    forming at least a portion of a rigid cannula tube into a curved portion having a bend radius at a particular location on the curved portion, wherein a cross-section of the curved portion at the particular location has an elongated shape with a long axis being generally perpendicular to the bend radius; and
    shaping the cross-section of the curved portion at the particular location into an oval shape, wherein a major axis of the oval shape is generally aligned with the bend radius at the particular location;
    wherein a portion of an interior wall of the curved portion at the particular location has a radius of curvature smaller than a radius of curvature of an outer circumference of a surgical instrument sized to contact the interior wall at the curved portion during insertion of the surgical instrument through the curved portion.

8. The method of claim 7, wherein the shaping of the cross section of the curved portion at the particular location comprises forming at least two spaced apart contact regions at the particular location so that the surgical instrument contacts an interior wall of the curved portion of the cannula tube at the two spaced apart contact regions when the surgical instrument is inserted through the curved portion, but does not contact the interior wall of the curved portion of the cannula tube between the two contact regions.

* * * * *